US005801173A

United States Patent [19]
Lohray et al.

[11] Patent Number: 5,801,173
[45] Date of Patent: Sep. 1, 1998

[54] HETEROCYCLIC COMPOUNDS HAVING ANTIDIABETIC, HYPOLIPIDAEMIC, ANTIHYPERTENSIVE PROPERTIES, PROCESS FOR THEIR PREPARATION AND PHARMACEUTICAL COMPOSITIONS CONTAINING THEM

[75] Inventors: Vidya Bhushan Lohray; Braj Bhushan Lohray; Sekar Reddy Alla; Rajagopalan Ramanujam; Ranjan Chakrabarti, all of Hyderabad, India

[73] Assignees: Dr. Reddy's Research Foundation, Hyderabad, India; Reddy-Cheminor, Inc., Ridgewood, N.J.

[21] Appl. No.: 687,840

[22] Filed: Jul. 26, 1996

[51] Int. Cl.⁶ ...................... C07D 417/12; A61K 31/425
[52] U.S. Cl. .......................... 514/252; 514/318; 514/342; 514/369; 544/364; 546/194; 546/280; 548/183
[58] Field of Search ........................... 548/183; 544/364; 546/280, 194; 514/252, 318, 342, 369

[56] References Cited

U.S. PATENT DOCUMENTS

| | | | |
|---|---|---|---|
| 4,342,771 | 8/1982 | Schnur | 424/263 |
| 4,367,234 | 1/1983 | Schnur | 424/272 |
| 4,725,610 | 2/1988 | Meguro | 514/369 |
| 4,873,255 | 10/1989 | Yoshioka | 514/369 |
| 5,002,953 | 3/1991 | Hindley | 514/275 |
| 5,036,079 | 7/1991 | Clark | 514/333 |
| 5,037,842 | 8/1991 | Goldstein | 514/375 |
| 5,130,379 | 7/1992 | Clark | 514/333 |
| 5,266,582 | 11/1993 | De Nanteuil | 514/367 |
| 5,296,605 | 3/1994 | De Nanteuil | |
| 5,330,999 | 7/1994 | De Nanteuil | |
| 5,420,146 | 5/1995 | Malamas | 514/364 |
| 5,468,762 | 11/1995 | Malamas | 514/376 |
| 5,478,851 | 12/1995 | Cantello | 514/369 |
| 5,478,852 | 12/1995 | Olefsky | 514/369 |
| 5,478,853 | 12/1995 | Regnier | 514/369 |
| 5,480,896 | 1/1996 | Malamas | 514/364 |
| 5,498,621 | 3/1996 | Dow | 514/369 |
| 5,521,202 | 5/1996 | Yano | 514/369 |

FOREIGN PATENT DOCUMENTS

| | | |
|---|---|---|
| 008203A | 2/1980 | European Pat. Off. |
| 0139421 | 5/1985 | European Pat. Off. |
| 155845A | 9/1985 | European Pat. Off. |
| 0207581 | 1/1987 | European Pat. Off. |
| 236624A | 9/1987 | European Pat. Off. |
| 0306228 | 3/1989 | European Pat. Off. |
| 0332331 | 9/1989 | European Pat. Off. |
| 0332332 | 9/1989 | European Pat. Off. |
| 0337819 | 10/1989 | European Pat. Off. |
| 0356214 | 2/1990 | European Pat. Off. |
| 0397453 | 11/1990 | European Pat. Off. |
| 0415605 | 3/1991 | European Pat. Off. |
| 0419035 | 3/1991 | European Pat. Off. |
| 0439321 | 7/1991 | European Pat. Off. |
| 0441605 | 8/1991 | European Pat. Off. |
| 0454501 | 10/1991 | European Pat. Off. |
| 0528734 | 2/1993 | European Pat. Off. |
| 0543662 | 5/1993 | European Pat. Off. |
| 0236624B | 10/1993 | European Pat. Off. |
| 590793A | 4/1994 | European Pat. Off. |
| 605228A | 7/1994 | European Pat. Off. |
| 645387A | 3/1995 | European Pat. Off. |
| 0678511 | 10/1995 | European Pat. Off. |
| 745600A | 12/1996 | European Pat. Off. |
| 62-175458 | 8/1987 | Japan. |
| 6452765 | 2/1989 | Japan. |
| 2558473 | 11/1996 | Japan. |
| 5355524 | 8/1984 | Spain. |
| 9112003 | 8/1991 | WIPO. |
| 9207838 | 5/1992 | WIPO. |
| 9207850 | 5/1992 | WIPO. |
| 9405659 | 3/1994 | WIPO. |
| 9425026 | 11/1994 | WIPO. |
| 9507697 | 3/1995 | WIPO. |
| 9535108 | 12/1995 | WIPO. |

OTHER PUBLICATIONS

Khan. A., et al., "Synthesis and Antibacterial Activity of Some New 2–aryloxymethyl–3–substituted–quinazolin–4 (3H)–ones" Pharmazie vol. 43, No. 12, pp. 864–865, 1988.
Chemical Abstracts, vol. 93, No. 17, Oct. 27, 1980, No. 168217.
Shukla, J.S., et al. "Synthesis of 2–phenoxymethyl–3–(2'–pyridyl/ thiazolyl)–4–quinazolones as Possible Antifertility Drugs" Indian Journal Chemical, vol. 17B, No. 6, pp. 651–652, Jun. 1979.
Husain, M.I., et al., "Some New 2–aryloxymethyl–3–.alpha.–substituted carboxymethyl–6, 8 substituted 4–quinazolones as Possible Anticonvulsants", Pharmazie, vol. 37, No. 6, 1982, pp. 408–410.
G. De Nanteuil, "Euglygaemic and Biological Activities of Novel Thiazolidine–2,4–dione Derivatives" Arzneittel Forschung/Drug Design, vol. 45, No. II, 1995, pp. 1176–1181.
Whitcomb, R.W., "Thiazolidinediones", Expert Opinion on Investigational Drugs, vol. 4, No. 12, Dec. 1995, pp. 1299–1309.
Behavioural Brain Research, 75 (1996) pp. 1–11, Messier, et al.
D.A. Clark et al. "Substituted Dihydrobenzopyran ... " J. Med. Chem. 1991, 34, 319–325.
R.L. Dow et al. "Benzyloxzolidine–2,4–diones ... " J. Med. Chem. 1991, 34, 1538–1544.
T. Sohda et al. "Studies on Antidiabetic ... " J. Med. Chem, 1992, vol. 35. No. 14, 2617–2626.
B. Hulin et al. "Novel Thiazolidine ... " J. Med. Chem., 1992, vol. 35, No. 10, 1853–1864.
S.W. Goldstein et al. "Hydroxyurea Derivatives ... " J. Med. Chem. 1993, 36, 2238–2240.
Journal of Medicinal Chemistry vol. 37, No. 23, 1994 Barrie, CC. et al. pp. 3977–3985.
Chemical and Pharmaceutical Bulletin vol. 30, No. 10, 1982 pp. 3580–3600, Takashi Sohda et al.

*Primary Examiner*—Robert Gerstl
*Attorney, Agent, or Firm*—Ladas & Parry

[57] ABSTRACT

Novel antidiabetic compounds, their tautomeric forms, their derivatives, their steroisomers, their polymorphs, their pharmaceutically acceptable salts, their pharmaceutically acceptable solvates and pharmaceuticaly acceptable compositions containing them; methods for preparing the antidiabetic compounds and their uses.

28 Claims, No Drawings

HETEROCYCLIC COMPOUNDS HAVING ANTIDIABETIC, HYPOLIPIDAEMIC, ANTIHYPERTENSIVE PROPERTIES, PROCESS FOR THEIR PREPARATION AND PHARMACEUTICAL COMPOSITIONS CONTAINING THEM

FIELD OF THE INVENTION

The present invention relates to novel antidiabetic compounds, their tautomeric forms, their derivatives, their stereoisomers, their polymorphs, their pharmaceutically acceptable salts, their pharmaceutically acceptable solvates and pharmaceutically acceptable compositions containing them. This invention particularly relates to novel thiazolidinedione derivatives of the general formula (I), their tautomeric forms, their derivatives, their stereoisomers, their polymorphs and their pharmaceutically acceptable salts, pharmaceutically acceptable solvates and pharmaceutical compositions containing them.

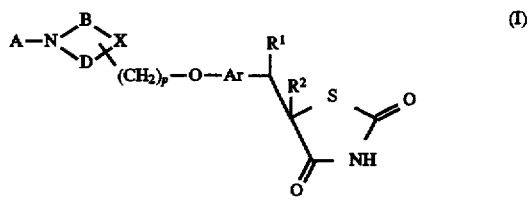

The present invention also relates to a process for the preparation of the above said novel, thiazolidinedione derivatives, their tautomeric forms, their stereoisomers, their polymorphs, their pharmaceutically acceptable salts, pharmaceutically acceptable solvates, novel intermediates and pharmaceutical compositions containing them.

The thiazolidinedione derivatives of the general formula (I) defined above of the present invention are useful for the treatment and/or prophylaxis of diseases in which insulin resistance is the underlying pathophysiological mechanism such as type II diabetes, impaired glucose tolerance, dyslipidaemia, hypertension, coronary heart disease and other cardiovascular disorders including atherosclerosis, insulin resistance associated with obesity and psoriasis; for treating diabetic complications and other diseases such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders; as aldose reductase inhibitors and for improving cognitive functions in dementia.

BACKGROUND OF THE INVENTION

The most significant and effective drug for the treatment of diabetes after the advent of the sulfonyl ureas has been the development of a group of compounds by Takeda, which are the derivatives of 5-(4-alkoxybenzyl)-2,4-thiazolidinediones of the formula (II) (Ref. Chem. Pharm. Bull. 1982,30,3580–3600). In the formula (II), V represents substituted or unsubstituted divalent aromatic group and U represents various groups which have been reported in various patent documents.

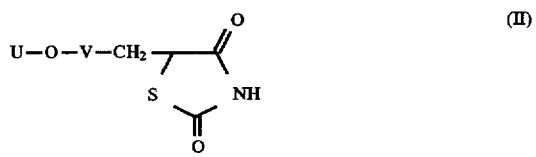

By way of examples, U may represent the following groups:

i) a group of the formula (IIa) where $R^1$ is hydrogen or hydrocarbon residue or heterocyclic residue which may each be substituted, $R^2$ is hydrogen or a lower alkyl which may be substituted by a hydroxy group, X is an oxygen or sulphur atom, Z is a hydroxylated methylene or a carbonyl, m is 0 or 1, and n is an integer of 1–3. These compounds have been disclosed in the European Patent Application No. 0 177 353

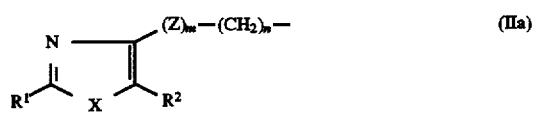

An example of these compounds is shown in formula (IIb)

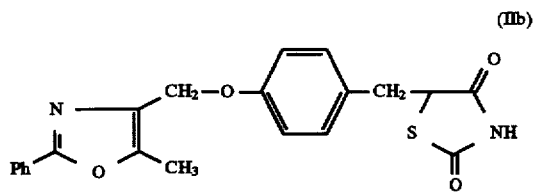

ii) a group of the formula (IIc) wherein $R^1$ and $R^2$ are the same or different and each represents hydrogen or $C_1$–$C_5$ alkyl, $R^3$ represents hydrogen, acyl group, a ($C_1$–$C_6$) alkoxycarbonyl group or aralkyloxycarbonyl group, $R^4$ and $R^5$ are same or different and each represent hydrogen, $C_1$–$C_5$ alkyl or $C_1$–$C_5$ alkoxy or $R^4$, $R^5$ together represent $C_1$–$C_4$ alkenedioxy group, n is 1, 2, or 3, and W represents $CH_2$, CO, or $CHOR^6$ group in which $R^6$ represents any one of the items or groups defined for $R^3$ and may be the same or different from $R^3$. These compounds are disclosed in the European Patent Application No. 0 139 421.

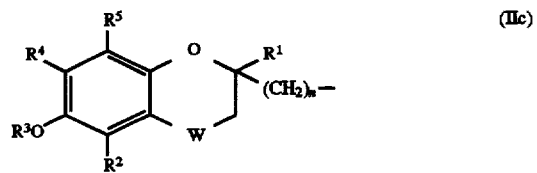

An example of these compounds is shown in (IId)

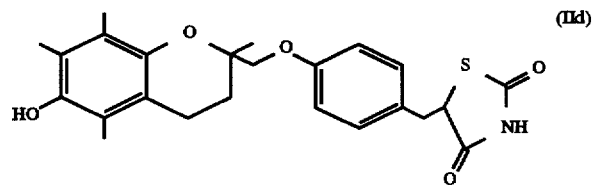

iii) A group of formula (IIe) where $A^1$ represents substituted or unsubstituted aromatic heterocyclic group, $R^1$ represents a hydrogen atom, alkyl group, acyl group, an aralkyl group wherein the aryl moiety may be substituted or unsubstituted, or a substituted or unsubstituted aryl group, and n represents an integer in the range from 2 to 6. These compounds are disclosed in European Patent No. 0 306 228.

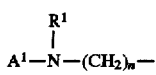

An example of this compound is shown in formula (IIf)

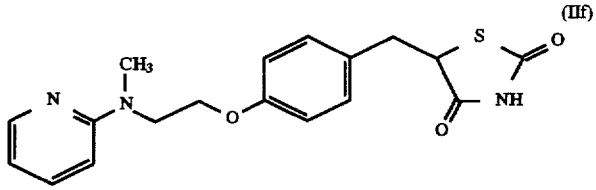

iv) A group of formula (IIg) where Y represents N or $CR^5$, $R^1$, $R^2$, $R^3$, $R^4$ and $R^5$ represents hydrogen, halogen, alkyl and the like and $R^6$ represents hydrogen, alkyl, aryl and the like, and n represents an integer of 0 to 3. These compounds are disclosed in European Patent Application No. 0 604 983.

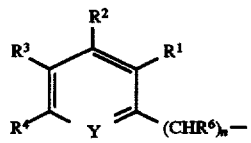

An example of this compound is shown in formula (IIh)

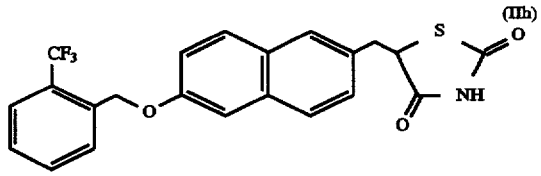

v) A group of formula (IIi a–d) where $R^1$ represents hydrogen atom, halogen, linear or branched $(C_1-C_6)$alkyl, $(C_1-C_6)$alkoxy, trifluoromethyl or cyano groups and X represents S, O or NR where R=H or $(C_1-C_6)$alkyl group. These compounds are disclosed in European Patent Application No. 0 528 734.

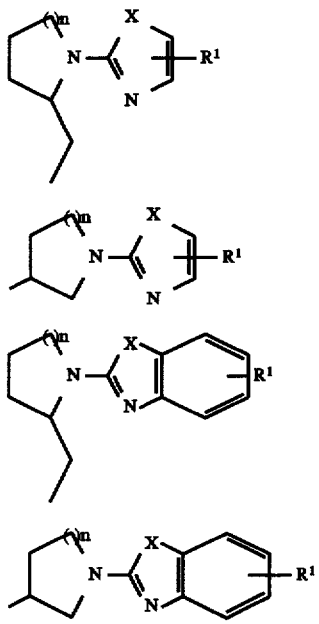

An example of this class of compound is shown in formula (IIj)

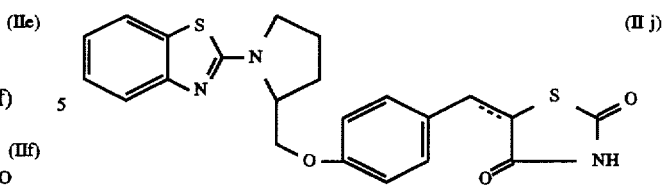

Some of the above referred hitherto known antidiabetic compounds seem to possess bone marrow depression, liver and cardiac toxicities or modest potency and consequently, their regular use for the treatment and control of diabetes is becoming limited and restricted.

SUMMARY OF THE INVENTION

With an objective of developing new compounds for the treatment of type II diabetes [non-insulin-dependent-diabetes mellitus (NIDDM)] which could be more potent at relatively lower doses and having better efficacy with lower toxicity, we focused our research efforts in a direction of incorporating safety and better efficacy, which has resulted in the development of novel thiazolidinedione derivatives having the general formula (I) as shown above.

The main objective of the present invention is therefore, to provide novel thiazolidinedione derivatives of formula (I), their tautomeric forms, their stereoisomers, their polymorphs, their pharmaceutically acceptable salts, their pharmaceutically acceptable solvates and pharmaceutical compositions containing them, or their mixtures.

Another objective of the present invention is to provide novel thiazolidinedione derivatives of formula (I), their tautomeric forms, their stereoisomers, their polymorphs, their pharmaceutically acceptable salts, their pharmaceutically acceptable solvates and pharmaceutical compositions containing them or their mixtures having enhanced activities, no toxic effect or reduced toxic effect.

DETAILED DESCRIPTION OF THE INVENTION

Thiazolidinedione derivatives of the present invention have the general formula (I)

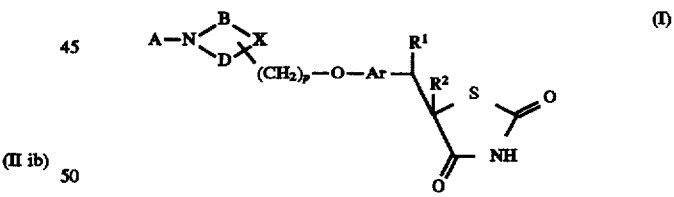

In the above formula (I), A represents substituted or unsubstituted aromatic group, a substituted or unsubstituted five membered heterocyclic group with one hetero atom selected from nitrogen, oxygen or sulfur, or a substituted or unsubstituted six membered heterocyclic group with one or more nitrogen atoms, which may or may not contain one or more oxo group on the ring, B and D represent substituted or unsubstituted linking group between N and X which may or may not contain one or more double bonds, X represents, either a $CH_2$ group or a hetero atom selected from the group of nitrogen, oxygen or sulfur, Ar represents an optionally substituted divalent aromatic or heterocyclic group, $R^1$ and $R^2$ can be the same or different and represent hydrogen atom, lower alkyl, halogen, alkoxy or hydroxy groups or $R^1$ and $R^2$ taken together represents a bond and p is an integer ranging from 0–4. A may be a six membered heterocyclic group which contains 1–3 nitrogen atoms and A may contain up to 3 oxo groups.

Suitable aromatic groups represented by A include phenyl, naphthyl, phenanthryl, preferably, phenyl and naphthyl group, suitable heterocyclic groups represented by A include furyl, pyrrolyl, thienyl, pyridyl, quinolyl, 4-pyridone-2-yl, pyrimidyl, 4-pyrimidone-2-yl, pyridazyl, and 3-pyridazone-2-yl groups, preferably, pyridyl and quinolyl group.

Suitable substituents on the aromatic and heterocyclic group represented by A include hydroxy, amino group, halogen atoms such as chlorine, fluorine, bromine, and iodine; substituted or unsubstituted ($C_1$–$C_{12}$) alkyl group, especially, ($C_1$–$C_6$)alkyl group, linear or branched, such as methyl, ethyl, n-propyl, isopropyl, iso-butyl, t-butyl, isobutyl, pentyl, and hexyl groups; ($C_3$–$C_6$)cycloalkyl group such as cyclopropyl, cyclobutyl, cyclopentyl, and cyclohexyl; cycloaminoalkyl groups such as morpholinyl, pyrrolidinyl, and piperidinyl; aryl group such as phenyl and naphthyl; aralkyl such as benzyl and phenethyl; heteroaryl group such as pyridyl, thienyl, furyl, tetrazolyl and the like, alkoxy groups such as methoxy and ethoxy; aryloxy such as phenoxy and benzyloxy; alkoxycarbonyl such as methoxycarbonyl and ethoxycarbonyl; aryloxycarbonyl group such as phenoxycarbonyl; amino ($C_1$–$C_6$) alkyl, hydroxy ($C_1$–$C_6$) alkyl, ($C_1$–$C_6$) alkoxy, thio($C_1$–$C_6$)alkyl, ($C_1$–$C_6$)alkylthio; acyl group such as acetyl, propionyl, benzoyl, carboxylic acid and its derivatives such as amides, like $CONH_2$, $CONHMe$, $CONMe_2$, $CONHEt$, $CONEt_2$, $CONHPh$ and the like; acyloxy group such as OCOMe, OCOEt, OCOPh and the like; sulfonic acid and its derivatives such as $SO_2NH_2$, $SO_2NHMe$, $SO_2NMe_2$, $SO_2NHCF_3$, and the like etc. These substituents may further be substituted by groups such as halogen, lower alkyl, lower alkoxy, hydroxy, amino and the like. The substituents on the adjacent carbon atoms on the group represented by A along with the carbon atoms to which they are attached may also form a substituted or unsubstituted, aromatic, saturated or unsaturated 5–7 membered cyclic structure which may be carbocylic or heterocyclic wherein one or more hetero atoms selected from N, O, and S such as phenyl, naphthyl, thienyl, furyl, oxazolyl, thiazolyl, furyl, imidazolyl, azacyclobutyl, isoxazolyl, azepinyl and the like, preferably, phenyl, furyl and imidazolyl groups. The substituents on such cyclic structure may be selected from the same group that may substitute the aromatic and heterocyclic group represented by A.

Suitable linking group between N and X represented by B may contain one to four carbon atoms, one to two being preferred and suitable linking group between N and X represented by D may contain zero to four carbon atoms, zero to two being preferred. The compounds according to Formula (I) always have a linking group B and a linking group D. The linking group D having no carbon atom means that the linking group D represents a bond. B and D may also contain zero to two double bonds, no double bond or one double bond being preferred. The substituents on B and D include hydroxy, amino, halogen such as chlorine, bromine, iodine; optionally substituted linear or branched ($C_1$–$C_2$) alkyl, especially ($C_1$–$C_6$) alkyl group such as methyl, hydroxymethyl, aminomethyl, methoxymethyl, trifluoromethyl, ethyl, isopropyl, hexyl etc.; ($C_3$–$C_6$) cycloalkyl groups such as cyclopropyl, fluorocyclopropyl, cyclobutyl, cyclopentyl, fluorocyclopentyl, cyclohexyl, fluorocyclohexyl and the like; ($C_1$–$C_6$) alkoxy, ($C_3$–$C_6$) cycloalkoxy, aryl such as phenyl; heterocyclic groups such as furyl, thienyl and the like; ($C_2$–$C_6$) acyl;($C_2$–$C_6$) acyloxy; hydroxy ($C_1$–$C_6$) alkyl; amino ($C_1$–$C_6$) alkyl; mono or di ($C_1$–$C_6$)alkylamino; cyclo ($C_2$–$C_5$)alkylamino groups; two substituents together with the adjacent carbon atoms to which they are attached may form a substituted or unsubstituted, aromatic, saturated or unsaturated 5–7 membered cyclic structure which may be carbocylic or heterocyclic wherein one or more hetero atoms are selected from N, O, and S such as phenyl, naphthyl, thienyl, furyl, oxazolyl, thiazolyl, furyl, azacyclobutenyl, isoxazolyl, azepinyl and the like. The substituents on such cyclic structure may be selected from the same group that may substitute the aromatic and heterocyclic group represented by A.

Suitable X includes $CH_2$, O, N or S group, preferably, $CH_2$ or O.

The group represented by Ar includes divalent phenylene, naphthylene, pyridyl, benzofuranyl, benzoxazolyl, benzothiazolyl, indolyl, indolinyl, azaindolyl and the like. The substituents on the group represented by Ar include linear or branched optionally halogenated ($C_1$–$C_6$)alkyl and ($C_1$–$C_3$)alkoxy, halogen, acyl, amino, acylamino, thio, carboxylic and sulfonic acids and their derivatives.

Suitable $R^1$ and $R^2$ include hydrogen, methyl, ethyl, fluorine, chlorine, bromine, iodine, methoxy, hydroxy or together represent a bond; preferably both $R^1$ and $R^2$ are hydrogen or together represent a bond.

Suitable p is an integer ranging from 0–4, preferably 0–2.

Pharmaceutically acceptable salts forming part of this invention include salts of the thiazolidinedione moiety such as alkali metal salts like Li, Na, & K salts and salts of carboxy group wherever appropriate, such as aluminum, alkali metal salts, alkaline earth metal salts, ammonium or substituted ammonium salts. Salts may include acid addition salts which are sulphates, nitrates, borates, hydrohalides, acetates, tartrates, maleates, citrates, succinates, palmoates, methanesulphonates, benzoates, ascorbates, glycerophosphates, ketoglutarates and the like. Pharmaceutically acceptable solvates may be hydrates or comprising other solvents of crystallization such as alcohols.

Particularly useful compounds according to the invention include 5-[4-[N-(2-pyridyl)-(2S)-2-pyrrolidinyl methoxy] phenylmethylene]-thiazolidine-2,4-dione and 5-[4-[N-(2-pyridyl)-(2S)-2-pyrrolidinyl methoxy]phenylmethyl]-thiazolidine-2,4-dione.

Still another objective of the present invention is to produce a process for the preparation of thiazolidinedione derivatives of the general formula (I) as defined above.

Yet another objective of the present invention is to provide pharmaceutical compositions containing the compound of the general formula (I), their tautomers, their stereoisomers, their polymorphs, their salts, solvates or their mixtures in combination with suitable carriers, diluents and other media normally employed in preparing such compositions.

Accordingly, the present invention provides a process for the preparation of novel thiazolidinedione derivatives of formula (I), their stereoisomers, their polymorphs, their tautomeric forms, their pharmaceutically acceptable salts, their pharmaceutically acceptable solvates, which comprises:

(a) reacting a compound of general formula (III)

$$A\text{—}L^1 \qquad\qquad (III)$$

where A is defined above and $L^1$ is a halogen atom such as chlorine, bromine or iodine; a thioalkyl group such as thiomethyl group, or a group capable of coupling with an amine nitrogen atom, with a compound of general formula (IV)

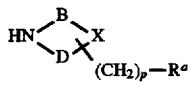

where B, D, X and p are as defined earlier and $R^a$ is a hydroxy group or a group which can be converted to a hydroxy group or a leaving group such as OMs, OTs, Cl, Br or I, by conventional methods, to yield a compound of general formula (V)

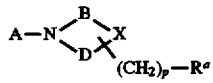

where A, B, D, $R^a$, X and p are as defined earlier.

The reaction of compound of general formula (III) with a compound of general formula (IV) to yield a compound of general formula (V) may be carried out in neat or in the presence of solvents such as DMF, DMSO, acetone, $CH_3CN$, THF, pyridine or ethanol. The inert atmosphere is maintained by using inert gases such as $N_2$, Ar or He. The reaction may be effected in the presence of a base such as $K_2CO_3$, $Na_2CO_3$, KOH, NaOH, NaH and the like. The amount of base may range from 1 to 20 equivalents, preferably 1–10 equivalents. The reaction may be carried out at a temperature in the range 20° C. to 180° C., preferably at a temperature in the range 50°–150° C. Duration of the reaction may range from 1 to 48 hours, preferably from 1 to 12 hours. In the reaction, the ratio of the compound of general formula (III) and (IV) may range from 1 to 20 equivalents, preferably from 1 to 5 equivalents.

(b) reacting the compound of general formula (V) where $R^a$ is a hydroxy group with a compound of general formula (VI)

where Ar is as defined earlier and $R^b$ is a halogen atom such as chlorine or fluorine, or $R^b$ is a hydroxy group to yield a compound of general formula (VII)

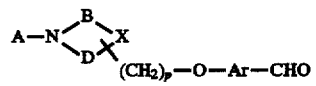

where A, B, D, X, Ar and p are as defined earlier.

The reaction of compound of general formula (V) where $R^a$ is a hydroxy group with the compound of general formula (VI) where $R^b$ is a halogen atom to give a compound of general formula (VII) may be carried out in the presence of solvents such as THF, DMF, DMSO, DME and the like. The inert atmosphere is maintained by using inert gases such as $N_2$, Ar, He. The reaction may be effected in the presence of a base such as $K_2CO_3$, $Na_2CO_3$, NaH. The reaction temperature may range from 20° C. to 120° C., preferably at a temperature in the range of 30° C. to 80° C. The duration of the reaction may range from 1 to 24 hours, preferably from 2 to 12 hours.

The reaction of compound of general formula (V) where $R^a$ is a hydroxy group with the compound of general formula (VI) where $R^b$ is a hydroxy group may be carried out using suitable coupling agents such as dicyclohexyl urea, $PPh_3$/DEAD and the like. The reaction may be carried out in the presence of solvents such as THF, DME, $CH_2Cl_2$, $CHCl_3$, toluene, acetonitrile, carbontetrachloride and the like. The inert atmosphere is maintained by using inert gases such as $N_2$, Ar, He. The reaction may be effected in the presence of DMAP-HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

(c) reacting the compound of general formula (VII) with 2,4-thiazolidinedione to yield a compound of general formula (VIII)

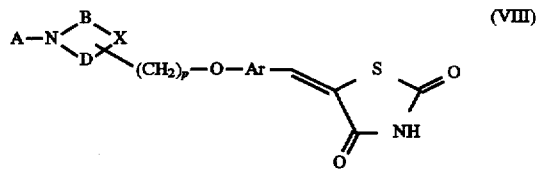

where A, B, D, X, Ar, p are defined earlier and removing the water formed during the reaction by conventional methods.

The reaction between the compound of general formula (VII) with 2,4-thiazolidinedione to give general formula (VIII) in step (c) may be carried out neat in the presence of sodium acetate or in the presence of a solvent such as benzene, toluene, or methoxyethanol. The reaction temperature may range from 80° C. to 140° C. depending upon the solvents employed. A suitable catalyst such as piperidinium acetate or benzoate, or sodium acetate may also be employed. The water produced in the reaction may be removed, for example, by using Dean Stark water is separator or by using water absorbing agents like molecular seives etc. And if desired, (d) reducing the compound of general formula (VIII) obtained in step (c) by known methods, to obtain the compound of general formula (IX)

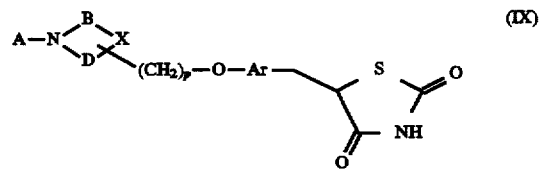

where A, B, D, X, Ar and p are as defined earlier.

The reduction of compound of general formula (VIII) obtained in step (c) to yield a compound of general formula (IX) may be carried out in the presence of gaseous hydrogen and a catalyst such as Pd/C, Rh/C, Pt/C, and the like. The reaction may also be conducted in the presence of solvents such as dioxane, acetic acid, ethyl acetate, THF, EtOH and the like. A pressure between atmospheric pressure and 80 psi may be employed. The catalyst may be 5–10% Pd/C and the amount of catalyst used may range from 50–150% w/w. The reaction may also be carried out by employing metal solvent reduction such as magnesium in methanol or sodium amalgam in methanol. And if desired, (e) resolving the compound of general formula (VIII) and of general formula (IX) into their stereoisomers and if desired, (f) converting the compound of the general formula (VIII) and compound of general formula (IX) obtained in step (c and d) respectively or the resolved stereoisomers thereof into their pharmaceutically acceptable salts, their pharmaceutically acceptable solvates by conventional methods.

In an embodiment of the invention, the compound of general formula (VII) can be prepared by converting the compound of general formula (V) to a compound of general formula (X)

where A, B, D, X and p are as defined earlier and $L^2$ is a leaving group such as halide group like chloride, bromide or iodide, or methanesulfonate, p-toluenesulfonate, trifluoromethane sulfonate and the like and further reaction of the compound of general formula (X) with a compound of general formula (VI) where Ar is as defined earlier and $R^b$ is a hydroxy group.

The compound of general formula (V) may be converted to a compound of general formula (X) using halogenating agents such as thionyl chloride, $CBr_4/PPh_3$, $CCl_4/PPh_3$, phosphorus halides or using p-toluenesulfonyl chloride, methanesulfonyl chloride, trifluoromethanesulfonyl chloride or anhydride in neat or in the presence of a base such as pyridine, triethyl amine etc. These reagents may be used in 1 to 4 equivalents, preferably 1 to 2 equivalents. Temperature in the range $-10°$ C. to $100°$ C. may be employed, preferably from 0C. to $60°$ C. The reaction may be conducted for 0.5 to 24 hours, preferably from 1 to 12 hours.

The reaction of compound of general formula (X) with a compound of general formula (VI) ($R^b$=OH) to produce a compound of general formula (VII) may be carried out in the presence of solvents such as THF, DMF, DMSO, DME and the like. The inert atmosphere is maintained by using inert gases such as $N_2$, Ar, or He. The reaction may be effected in the presence of a base such as $K_2CO_3$, $Na_2CO_3$, or NaH. The reaction temperature may range from $20°$ C.–$120°$ C., preferably at a temperature in the range of $30°$ C.–$80°$ C. The duration of the reaction may range from 1–24 hours, preferably from 2 to 12 hours.

In another embodiment of this invention, the compound of general formula (VII) can also be prepared by reacting a compound of general formula (XI)

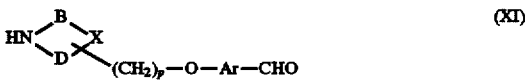

where B, D, X, Ar and p are as defined earlier, with a compound of general formula (III).

The reaction of compound of general formula (XI) with a compound of general formula (III) may be carried out neat or in the presence of solvents such as DMF, DMSO, acetone, acetonitrile or ethanol. The inert atmosphere is maintained by using inert gases such as $N_2$, Ar or He. The reaction may be effected in neat or in the presence of base such as $K_2CO_3$, $Na_2CO_3$, KOH, NaOH, NaH and the like. The amount of base may range from 1 to 20 equivalents, preferably 1–10 equivalents. The reaction may be carried out at a temperature in the range $20°$ C. to $180°$ C., preferably at a temperature in the range $50°$–$150°$ C. Duration of the reaction may range from 1 to 48 hours, preferably from 1 to 12 hours. The amounts of the compound of general formula (III) and (XI) may range from 1 to 20 equivalents preferably from 1 to 5 equivalents.

The compound of general formula (XI) in turn can be prepared by reacting a compound of general formula (XII)

where B, D, X, Ar and p are as defined earlier and $R^3$ is a protecting group and $R^a$ is a leaving group with a compound of general formula (VI) ($R^b$=OH) followed by removal of N-protecting group using conventional methods.

The reaction of compound of general formula (VI) ($R^b$=OH) with a compound of general formula (XII) may be carried out in the presence of solvents such as THF, DMF, DMSO, DME and the like. The inert atmosphere is maintained by using inert gases such as $N_2$, Ar, or He. The reaction may be effected in the presence of a base such as $K_2CO_3$, $Na_2CO_3$, or NaH. The reaction temperature may range from $20°$ C. to $120°$ C., preferably at a temperature in the range of $30°$ C. to $80°$ C. The duration of the reaction may range from 1 to 12 hours, preferably from 2 to 6 hours. The N-protecting group $R^3$ is usually removed either by acid treatment or by hydrogenation or in the presence of a suitable base depending upon the nature of the protecting group employed.

In yet another embodiment of the present invention, the compound of the general formula (I), their tautomeric forms, their stereoisomers, their polymorphs, their pharmaceutically acceptable salts and their pharmaceutically acceptable solvates can also be prepared by reacting a compound of the general formula (V) where $R^a$ is OH group obtained and defined above with a compound of general formula (XIII) using a suitable coupling agent such as dicyclohexyl urea, $Ph_3P/DEAD$ and the like.

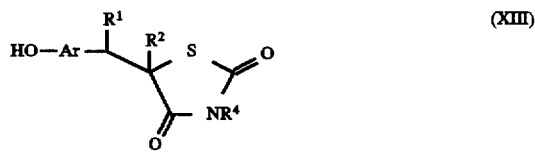

where $R^1$, $R^2$ and Ar are as defined earlier and $R^4$ is hydrogen or a nitrogen protecting group such as acyl or triarylmethyl group.

The reaction of compound of general formula (V) with a compound of general formula (XIII) may be carried out in the presence of solvents such as THF, DME, $CH_2Cl_2$, $CHCl_3$, toluene, acetonitrile, carbontetrachloride and the like. The inert atmosphere is maintained by using inert gases such as $N_2$, Ar, or He. The reaction may be effected in the presence of DMAP-HOBT and they may be used in the range of 0.05 to 2 equivalents, preferably 0.25 to 1 equivalents. The reaction temperature may be in the range of $0°$ C. to $100°$ C., preferably at a temperature in the range of $20°$ C. to $80°$ C. The duration of the reaction may range from 0.5 to 24 hours, preferably from 6 to 12 hours.

In still another embodiment of the present invention, the compound of the general formula (I), their tautomeric forms, their stereoisomers, their polymorphs, their pharmaceutically acceptable salts and their pharmaceutically acceptable solvates can also be prepared by reacting a compound of the general formula (X) obtained and defined above with a compound of general formula (XIII) as defined above.

The reaction of compound of general formula (X) with the compound of general formula (XIII) may be carried out in the presence of solvents such as THF, DMF, DMSO, DME and the like. The inert atmosphere is maintained by using inert gases such as $N_2$, Ar, or He. The reaction may be effected in the presence of a base such as $K_2CO_3$, $Na_2CO_3$, or NaH. The reaction temperature may range from $20°$ C.–$120°$ C., preferably at a temperature in the range of $30°$ C.–$80°$ C. The duration of the reaction may range from 1–24 hours, preferably from 2 to 12 hours.

In still another embodiment of the present invention, the compound of general formula (I) defined above can be obtained by reacting a compound of general formula (XIV)

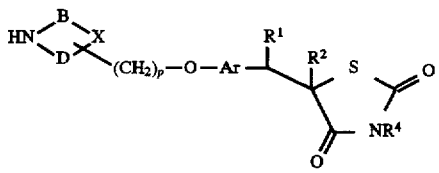

(XIV)

where B, D, $R^1$, $R^2$, $R^4$, X, Ar and p are as defined earlier, with a compound of general formula (III) defined above.

The reaction of compound of general formula (XIV) with the compound of general formula (III) to produce a compound of general formula (I) may be carried out neat or in the presence of solvents such as DMF, DMSO, acetone, acetonitrile, ethanol and THF. The inert atmosphere is maintained by using inert gases such as $N_2$, Ar, or He. The reaction may be effected in the presence of base such as $K_2CO_3$, $Na_2CO_3$, KOH, NaOH, NaH and the like. The amount of base may range from 1 to 20 equivalents, preferably 1–6 equivalents. The reaction may be carried out at a temperature in the range 20° C. to 180° C. preferably at a temperature in the range 50°–150° C. Duration of the reaction may range from 1 to 48 hours, preferably from 1 to 12 hours. The amounts of the compounds of general formula (III) and (XIV) may range from 1 to 20 equivalents preferably from 1 to 5 equivalents.

According to a feature of the invention there is provided a process for the preparation of novel intermediates of general formula (XIV) which comprises reacting a compound of general formula (XIII) with a compound of general formula (XV)

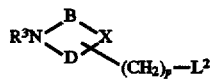

(XV)

where B, D, $R^3$, X, $L^2$, and p are as defined earlier, followed by removal of protecting group by conventional methods.

The reaction of compound of general formula (XIII) with the compound of general formula (XV) may be carried out in the presence of solvents such as THF, DMF, DMSO, DME and the like. The inert atmosphere is maintained by using inert gases such as $N_2$, Ar, or He. The reaction may be effected in the presence of a base such as $K_2CO_3$, $Na_2CO_3$, or NaH. The reaction temperature may range from 20° C. to 120° C., preferably at a temperature in the range of 30° C. to 80° C. The duration of the reaction may range from 1 to 12 hours, preferably from 2 to 6 hours.

According to another embodiment of the present invention the compound of the general formula (XIV), where $R^1$ and $R^2$ together represent a bond can also be prepared by reacting a compound of general formula (XVI)

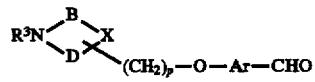

(XVI)

where B, D, Ar, X and p are defined as earlier and $R^3$ is a protecting group excluding A—$(CH_2)_k$—O—C(=Y)— where A represents aryl or heteroaryl group, k is an integer ranging between 1–4 and Y is a heteroatom selected from O, S or NR where R may be H or lower alkyl or alkoxy group, with 2,4-thiazolidinedione; followed by removal of N-protecting group by conventional methods.

The reaction between the compound of general formula (XVI) with 2,4-thiazolidinedione may be carried out neat in the presence of sodium acetate or in the presence of a solvent such as benzene, toluene, or methoxyethanol. The reaction temperature may range from 80° C. to 140° C. depending upon the solvents employed. A suitable catalyst such as piperidinium acetate or benzoate, or sodium acetate may also be employed. The water produced in the reaction may be removed, for example, by using Dean Stark water separator or by using water absorbing agents like molecular seives.

Conventional deprotection methods include treatment with acid such as, hydrochloric acid, trifluoroacetic acid or bases such as, KOH, NaOH, $Na_2CO_3$, $NaHCO_3$, or $K_2CO_3$ and the like. These reagents may be used as aqueous solution or as solutions in alcohols like methanol, ethanol etc. Deprotection can also be effected by gaseous hydrogen in the presence of catalyst such as Pd/carbon or conventional transfer hydrogenation methods.

The pharmaceutically acceptable salts are prepared by reacting the compound of formula (I) with one equivalent of a base such as sodium hydroxide, sodium methoxide, or sodium hydride in solvents like ether, THF etc. Alternatively, they are prepared by treatment with acids such as hydrochloric acid, hydrobromic acid, p-toluenesulphonic acid, methanesulfonic acid, acetic acid, citric acid, maleic acid and the like in solvents like ethyl acetate, ether, alcohols etc.

The stereoisomers of the compounds forming the part of this invention may be prepared by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, L-proline and the like or chiral bases such as brucine, cinchona alkaloids and their derivatives and the like.

The present invention also provides a pharmaceutical composition, containing the compounds of the general formula (I), as defined above, their tautomeric forms, their stereoisomers, their polymorphs, their pharmaceutically acceptable salts, their pharmaceutically acceptable solvates in combination with the usual pharmaceutically employed carriers, diluents and the like. The thiazolidinedione derivatives of the general formula (I) defined above of the present invention are useful for the treatment and/or prophylaxis of diseases in which insulin resistance is the underlying pathophysiological mechanism such as type II diabetes, impaired glucose tolerance, dyslipidaemia, hypertension, coronary heart disease and other cardiovascular disorders including atherosclerosis, insulin resistance associated with obesity and psoriasis; for treating diabetic complications and other diseases such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders; as aldose reductase inhibitors and for improving cognitive functions in dementia. The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carrier, diluent or solvent.

The compound of the formula (I) as defined above are clinically administered to mammals, including humans, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 200 mg/kg body weight of the subject per day or preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts of the compounds. The injectable solutions prepared in this manner can then be administered intravenously, intraperitoneally, subcutaneously, or intramuscularly, with intramuscular administration being preferred in man.

The invention is described in detail in the examples given below which are provided by way of illustration only and therefore should not be construed to limit the scope of the invention.

PREPARATION 1

N-(2-Pyridyl)-(2S)-2-pyrrolidinemethanol

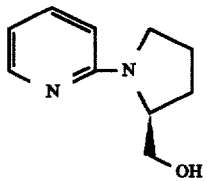

A mixture of 2-chloropyridine (118 g) and L-prolinol (70 g) was heated under nitrogen atmosphere at 160° C. with stirring for 4 h. The mixture was cooled to room temperature and poured into water and the solution was extracted with chloroform repeatedly. The combined organic extracts were dried (Na$_2$SO$_4$) and concentrated. The crude product was purified by column chromatography using 2% MeOH in CHCl3 as eluent to get 67.3 g (54.5%) of the title compound as a syrupy liquid.

$^1$H NMR (CDCl$_3$, 200 MHz): δ1.7 (m, 1H), 2.05 (m, 3H), 3.2–3.8 (m, 4H), 4.25 (m, 1H), 6.43 (d, J=8.4 Hz, 1H), 5.58 (t, J=6.0 Hz, 1H), 7.5 (m, 1H), 8.02 (d, J=4.2 Hz, 1H).

PREPARATION 2

N-(2-Pyridyl)-4-piperidinol

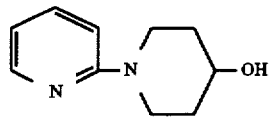

The title compound (3.5 g, 50%) was prepared as a semi solid from 2-chloropyridine (6.7 g) and 4-piperidinol (4 g) by an analogous procedure to that described in preparation 1.

$^1$H NMR (CDCl$_3$, 200 MHz): δ1.6 (m, 2H), 2.0 (m, 2H), 3.15 (m, 2H), 3.9 (m, 1H), 4.1 (m, 2H), 6.59 (m, 1H), 6.67 (d, J=8.6 Hz, 1H), 7.45 (m, 1H), 8.17 (d, J=3.6 Hz, 1H).

PREPARATION 3

N-(2-Pyridyl)-4-piperidinemethanol

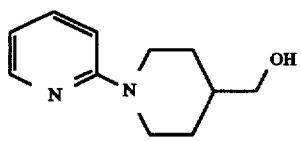

The title compound (2.7 g, 80%) was prepared as a syrupy liquid from 2-chloropyridine (6.5 ml) and 4-piperidinyl methanol (2 g) by an analogous procedure to that described in preparation 1.

$^1$H NMR (CDCl$_3$, 200 MHz): δ1.3 (m, 2H), 1.8 (m, 3H), 2.84 (t, J=11.7 Hz, 2H), 3.54 (d, J=6.2 Hz, 2H), 4.32 (approx. d, J=13 Hz, 2H), 6.59 (t, J 5.9 Hz, 1H), 6.67 (d, J=8.8 Hz, 1H), 7.46 (m, 1H), 8.18 (d, J=3.6 Hz, 1H).

PREPARATION 4

N-(2-Pyridyl)-4-piperidine methanesulphonate

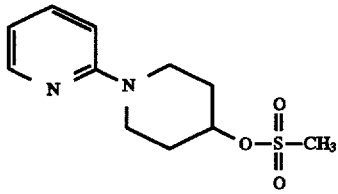

To an ice cooled solution of the product obtained in the preparation 2 (3.25 g) and triethylamine (8 ml) in dichloromethane (30 ml) at ca 0° C. was added methanesulphonyl chloride (1.7 ml). The mixture was stirred for 12 h at room temperature. At the end of this time, the reaction mixture was washed with water, dried (CaCl$_2$) and concentrated to get 4.7 g (100%) of the title compound. mp 66°–68° C.

$^1$H NMR (CDCl$_3$, 200 MHz)δ1.8–2.2 (m, 4H), 3.06 (s, 3H), 3.4 (m, 2H), 3.9 (m, 2H), 5.0 (m, 1H), 6.7 (m, 2H), 7.5 (m, 1H), 8.18 (d, J=3.6 Hz, 1H).

PREPARATION 5

N-(2-Pyridyl)-4-piperidinemethyl methanesulphonate

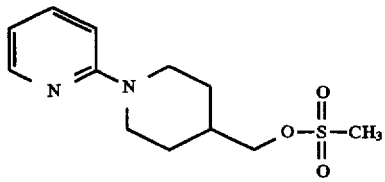

The title compound (2.1 g, 83%) was prepared as a semi solid from N-(2-pyridyl)-4-piperidinemethanol (1.8 g), obtained in preparation 3 and methanesulphonyl chloride (0.8 ml) by a similar procedure to that used in preparation 4.

$^1$H NMR (CDCl$_3$, 200 MHz): δ1.35 (m, 2H), 1.8–2.15 (m, 3H), 2.85 (t, J=12.2 Hz, 2H), 3.02 (s, 3H), 4.1 (d, J=6.2 Hz, 2H), 4.35 (approx. d, J=12.8 Hz, 2H), 6.6 (m, 2H), 7.48 (t, =7.8 Hz, 1H), 8.18 (d, J=3.8 Hz, 1H).

PREPARATION 6

4-[N-(Ethoxycarbonyl)-4-piperidinyloxy] benzaldehyde

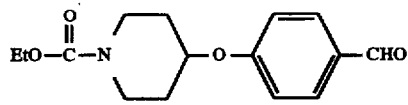

To a mixture of N-(ethoxycarbonyl)-piperidine-4-methanesulphonate (10 g) and 4-hydroxy benzaldehyde (5.8 g) in dry DMF (75 ml), K$_2$CO$_3$ (11 g) was added and the mixture was stirred at 80° C. for 12 h. At the end of this time, the reaction mixture was cooled, added water and extracted with EtOAc. The EtOAc extract was washed with 5% aqueous Na$_2$CO$_3$ solution followed by brine and dried over anhydrous sodium sulphate. The solvent was then removed by distillation under reduced pressure to give 7 g (63.6%) of the title compound as a semi solid.

$^1$H NMR (CDCl$_3$, 200 MHz): δ1.28 (t, J=7 Hz, 3H), 1.7–2.1 (m, 4H), 3.45 (m, 2H), 3.75 (m, 2H), 4.15 (q, J=7 Hz, 2H), 4.63 (m, 1H), 7.01(d, J=8.6 Hz, 2H), 7.84 (d, J=8.8 Hz, 2H), 9.39 (s, 1H).

PREPARATION 7

4-(4-Piperidinyloxy)benzaldehyde

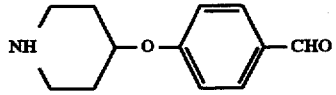

A mixture of the compound obtained in preparation 6 (4.5 g) and conc. HCl (40 ml) was stirred at 100° C. for 12 h. The reaction mixture was concentrated in vacuo. The residue was diluted with water, neutralized with saturated aqueous NaHCO$_3$ solution and extracted with CHCl$_3$, dried (CaCl$_2$) and concentrated in vacuo to get 3 g of the (90%) title compound as a semi solid.

$^1$H NMR (CDCl$_3$, 200 MHz): δ1.75 (m, 2H), 2.05 (m, 2H), 2.75 (m, 2H), 3.2 (m, 2H), 4.55 (m, 1H), 7.01 (d, J=8.6 Hz, 2H), 7.83 (d, J=8.6 Hz, 2H), 9.89 (s,1H).

PREPARATION 8

4-[N-(2-Pyridyl)-(2S)-2-pyrrolidinyl]methoxy benzaldehyde

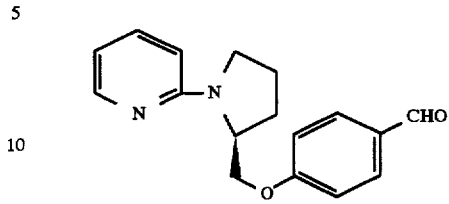

A solution of 40 g of the product obtained in preparation 1 in 300 ml of dimethyl formamide was added dropwise while cooling to a suspension of 16.1 g of 60% W/W dispersion of sodium hydride in 300 ml of dimethyl formamide. The mixture was then stirred for 1 h at room temperature, after which 47.7 mL of 4-fluorobenzaldehyde in 200 ml of dimethylformamide was added dropwise at room temperature. The reaction mixture was then stirred at 80° C. for 4 h. At the end of this time, water was added to the reaction mixture. The mixture was extracted with EtOAc and dried over anhydrous sodium sulphate. The solvent was evaporated to dryness under reduced pressure. The crude product was chromatographed on silica gel using 5–10% (gradient elution) of EtOAc in petroleum ether to afford 42.5 g (67%) of the title compound as a semi solid.

$^1$H NMR (CDCl$_3$, 200 MHz) : δ 2.1 (m, 4H), 3.3 (m, 1H), 3.5 (m, 1H), 3.96 (t, J=8.7 Hz, 1H), 4.4 (dd, J=9.6 and 3.4 Hz, 1H), 4.55 (m, 1H), 6.41 (d, J =8.8 Hz, 1H), 6.59 (m, 1H), 7.13 (d, J=8.8 Hz, 2H), 7.46 (m, 1H), 7.82 (d, J=8.8 Hz, 2H), 8.18 (d, J=3.8 Hz, 1H), 9.87 (s, 1H).

PREPARATION 9

4-[N-(2-Pyridyl)-4-piperidinyloxy]benzaldehyde

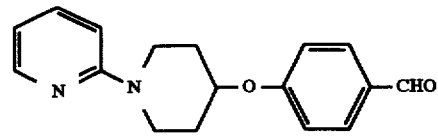

Method A: To a mixture of N-(2-pyridyl)-4-piperidine methanesulphonate (4.5 g) obtained in preparation 4 and 4-hydroxybenzaldehyde (2.5 g) in dry DMF (30 ml), K$_2$CO$_3$ (9.7 g) was added and the mixture was stirred at 80° C. for 10 h. At the end of this time, the reaction mixture was cooled, added water and extracted with EtOAc. The EtOAc extract was washed with 5% aqueous Na$_2$CO$_3$ solution followed by brine and dried over anhydrous sodium sulphate. The solvent was then removed by distillation under reduced pressure to give. 1.8 g (36.3%) of the title compound. mp 114°–116° C.

Method B: The title compound (0.6 g, 43%) was also prepared as a pale yellow soild (mp 114°–116° C.) from 4-(4-piperidinyloxy)benzaldehyde (1.0 g) obtained in preparation 7 and 2-chloropyridine (3.6 ml) by an analogous procedure to that described in preparation 1.

$^1$H NMR (CDCl$_3$, 200 MHz): δ1.9 (m, 2H), 2.1 (m, 2H), 3.5 (m, 2H), 3.9 (m, 2H), 4.7 (m, 1H), 6.7 (m, 2H), 7.03 (d, J=8.6 Hz, 2H), 7.49 (m, 1H), 7.85 (d, J=8.8 Hz, 2H), 8.2 (d, J=3.4 Hz, 1H), 9.89 (s, 1H).

PREPARATION 10

4-[N-(2-Pyridyl)-4-piperidinyl]methoxy benzaldehyde

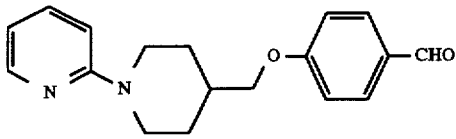

The title compound (1.0 g, 45%) was prepared as a semi solid from N-(2-pyridyl)-4-piperidinemethyl methanesulphonate (2.0 g) obtained in preparation 5 and 4-hydroxybenzaldehyde (1.1 g) by an analogous procedure to that described in method A of preparation 9.

$^1$H NMR (CDCl$_3$, 200 MHz): δ1.45 (m, 2H), 1.8–2.25 (m, 3H), 2.89 (m, 2H), 3.92 (d, J=6.2 Hz, 2H), 4.36 (approx. d, J=12.8 Hz, 2H), 6.62 (m, 2H), 6.99 (d, J =8.6 Hz, 2H), 7.47 (m, 1H), 7.83 (d, J=8.6 Hz, 2H), 8.19 (d, J=3.6 Hz, 1H), 9.88 (s, 1H).

PREPARATION 11

4-[2-[4-(2-Pyridyl)-1-piperazinyl]ethoxy] benzaldehyde

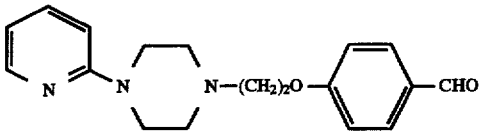

The title compound (2.0 g, 84%) was prepared as a thick liquid from 2-[4-(2-pyridyl)-1-piperazinyl]ethylchloride, HCl salt (2g) and 4-hydroxybenzaldehyde (1.4 g) in a similar manner to that described in Method A of preparation 9.

$^1$H NMR (CDCl$_3$, 200 MHz): δ2.78 (t, J=4.6 Hz, 4H), 2.96 (t, J=5.6 Hz, 2H), 3.64 (t, J=5 Hz, 4H), 4.29 (t, J=5.4 Hz, 2H), 6.66 (m, 2H), 7.03 (d, J=8.6 Hz, 2H), 7.5 (m, 1H), 7.85 (d, J=8.6 Hz, 2H), 8.2 (d, J=3.8 Hz, 1H), 9.9 (s, 1H).

EXAMPLE 1

5-[4-[N-(2-Pyridyl)-(2S)-2-pyrrolidinyl methoxy]phenylmethylene]thiazolidine-2,4-dione

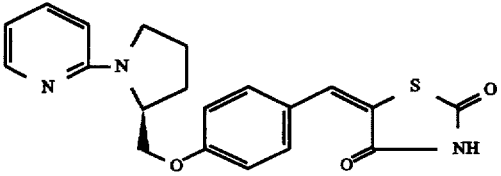

A solution of 4-[N-(2-pyridyl)-(2S)-2-pyrrolidinyl methoxy]benzaldehyde (33.5 g) obtained in preparation 8 and 2,4-thiazolidinedione (16.7 g) in toluene (300 ml) containing piperidine (1.5 g) and benzoic acid (1.8 g) was heated at reflux for 1 h using a Dean stark water separator. The reaction mixture was cooled and filtered, the filtrate was washed with H$_2$O, dried (Na$_2$SO$_4$) and evaporated under reduced pressure. The crude product was triturated with methanol and filtered to afford 27.5 g (60%) of the title compound mp 164° C.

$^1$H NMR (CDCl$_3$, 200 MHz): δ2.15 (m, 4H), 3.30 (m, 1H), 3.55 (m, 1H), 3.79 (t, J=9.2 Hz, 1H), 4.35 (dd, J=9.0 and 3.2 Hz, 1H), 4.6 (m, 1H), 6.47 (d, J=8.4 Hz, 1H), 6.65 (t, J=6.8 Hz, 1H), 7.01 (d, J=8.8 Hz 2H), 7.31 (d, J=8.8 Hz, 2H), 7.48 (s, 1H), 7.56 (t, J=6Hz, 1H), 7.16 (d, J=3.8 Hz, 1H).

EXAMPLE 2

5-[4-[N-(2-Pyridyl)-(2S)-2-pyrrolidinyl methoxy]phenylmethyl]thiazolidine-2,4-dione

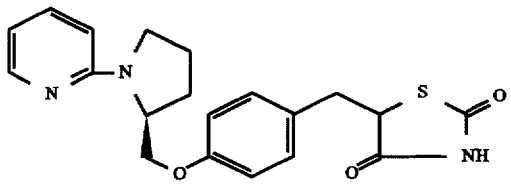

To a stirred suspension of the product obtained in the example 1 (10 g) in methanol (250 mL) at room temperature was added magnesium turnings (10.8 g) and the reaction mixture was stirred at room temperature for 4 hours. The reaction mixture was added to ice water (100 ml), the pH was adjusted to 6.5–7 using aqueous hydrochloric acid and the solution was extracted with chloroform (3×150 ml). The combined organic extract was washed with H$_2$O, dried (CaCl$_2$) and the solvent was removed under reduced pressure. The residual mass was chromatographed on silica gel using 0.5% methanol in chloroform to give 6.5 g (65%) of the title compound. mp 78°–80° C.

$^1$H NMR (CDCl$_3$, 200 MHz): δ2.1 (m, 4H), 3.05 (m, 1H), 3.2–3.6 (m, 3H), 3.82 (t, J=8.8 Hz, 1H), 4.15 (m, 1H), 4.45 (m, 2H), 6.44 (d, J=8.6 Hz, 1H), 6.56 (t, J=6 Hz, 1H), 6.9 (d, J=8.4 Hz, 2H), 7.15 (d, J=8.4 Hz, 2H), 7.46 (m, 1H), 8.14 (d, J=2.4 Hz, 1H).

EXAMPLE 3

5-[4-[N-(2-Pyridyl)-4-piperidinyloxy]phenyl methylene]thiazolidine-2,4-dione

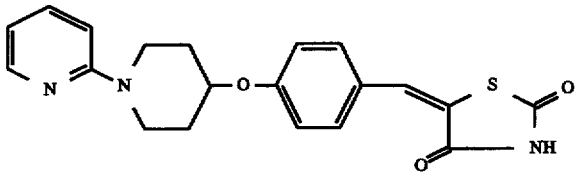

The title compound (1.5 g, 74%) was prepared from 4-[N-(2-pyridyl)-4-piperidinyloxy]benzaldehyde (1.5 g), obtained in preparation 9, by a similar procedure to that described in example 1. mp 218°–20 ° C.

$^1$H NMR (CDCl$_3$+DMSO-d$_6$, 200 MHz): δ1.9 (m, 2H), 2.1 (m, 2H), 3.5 (m, 2H), 3.9 (m, 2H), 4.65 (m, 1H), 6.62 (t, J=5.9 Hz, 1H), 6.72 (d, J=8.6 Hz, 1H), 7.02 (d, J=8.4 Hz, 2H), 7.5 (m. 3H), 7.74 (s, 1H), 8.18 (d, J=4 Hz, 1H).

EXAMPLE 4

5-[4-[N-(2-Pyridyl)piperidin-4-methoxy]phenylmethylene]thiazolidine-2,4-dione

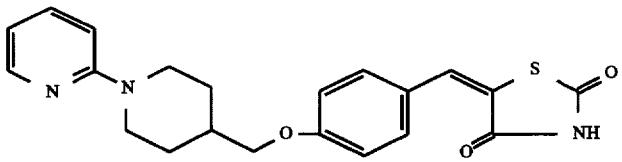

The title compound (0.46 g, 63%) was prepared from 4-[N-(2-pyridyl)piperidin-4-methoxy]benzaldehyde (0.55 g) obtained in preparation 10 by a similar procedure to that described in example 1. mp 233.4° C.

$^1$H NMR (CDCl$_3$, 200 MHz): δ1.45 (m, 2H), 1.9–2.2 (m, 3H), 2.9 (t, J=11.7 Hz, 2H), 3.9 (d, J=6.2 Hz, 2H), 4.38 (approx. d, J=13 Hz, 2H), 6.61 (t, J=5.8 Hz, 1H), 6.71 (d, J=8.6 Hz, 1H), 6.99 (d, J=8.8 Hz, 2H), 7.5 (m, 3H), 7.75 (s, 1H), 8.18 (d, J=3.8 Hz, 1H).

EXAMPLE 5

5-[4-[2-[4-(2-Pyridyl)-1-piperazinyl]ethoxy]phenylmethylene]thiazolidine-2,4-dione

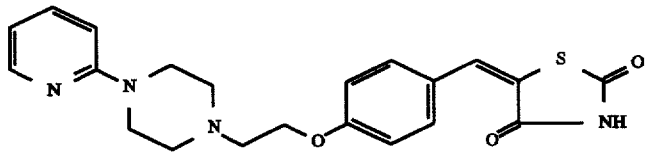

The title compound (0.85 g 64%) was prepared from 4-[2-[4-(2-pyridyl)-1-piperazinyl]ethoxy]benzaldehyde (1.0 g), obtained in preparation 11, by a similar prodcedure to that described in example 1. mp 158°–60° C.

$^1$H NMR (DMSO-d$_6$, 200 MHz): δ2.88 (m, 4H), 2.98 (m, 2H), 3.65 4H), 4.25 (m, 2H), 6.67 (m, 2H), 6.92 (d, J=8.4 Hz, 2H), 7.33 (d, J=8.6 Hz, 2H), 7.48 (m, 2H), 8.2 (d, J=3.6 Hz, 1H).

EXAMPLE 6

5-[4-[N-(2-Pyridyl)-(2S)-2-pyrrolidinyl methoxy]phenylmethylene]thiazolidine-2,4-dione, maleic acid salt

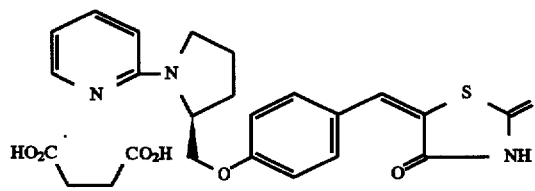

A solution of the product (50 g) obtained example 1 and maleic acid (16.7 g) in dry acetone (2L) was stirred at room temperature for 20 h. At the end of this time, the resulting solid was filtered, washed with cold acetone (2×200 ml) and dried under reduced pressure to get 52 g (80%) of the title compound. mp 132° C.

$^1$H NMR (DMSO-d$_6$, 200 MHz): δ2.13 (bs, 4H), 3.34 (m, 1H), 3.56 (m, 1H), 4.05 (m, 1H), 4.28 (dd, J=9.6 and 3.8 Hz, 1H), 4.53 (bs, 1H), 6.25 (s, 2H), 6.76 (m, 2H), 7.19 (d, J=8.8 Hz, 2H), 7.59 (d, J=8.8 Hz, 2H), 7.72 (m, 1H), 7.79 (s, 1H), 8.13 (d, J=4.2 Hz, 1H), 12.6 (bs, exchangeable with D$_2$O, 1H)

The compounds of the present invention showed blood sugar and triglycerides lowering activites through improving insulin resistance which has been demonstrated by the following in vivo experiment.

Male C57BL/KsJ-db/db mice of 8 to 14 weeks age, having body weight range of 35 to 60 grams, procured from the Jackson Laboraotory, USA, were used in the experiment. The mice were provided with standard feed (National Institute of Nutrition, Hyderabad, India) and acidified water,ad libitum. The animals having more than 300 mg/dl blood sugar were used for testing. The number of animals in each group was 4.

The random blood sugar and triglyceride levels were measured by collecting blood (100 μl) through orbital sinus, using heparinised capillary in EDTA containing tubes. This was centrifuged to obtain plasma. The plasma glucose and triglycerides levels were measured spectrometrically, by glucose oxidase and glycerol-3-PO$_4$ oxidase/peroxidase enzyme (Dr Reddy's Lab. Diagnostic Division Kits, Hyderabad, India) methods respectively. On 6th and 9th day the blood samples were collected one hour after administration of test compounds/vehicle for assessing the biological activity.

Test compounds were suspended on 0.5% carboxymethyl cellulose and administered to test group at a dose of 100 mg/kg through oral gavage daily for 6 days or 10 days. The control group received vehicle (dose 10 ml/kg). Troglitazone (100 mg/kg) has been used as standard which showed 28% and 26% reduction in random blood sugar level on 6th day and 9th day respectively and 50% reduction in plasma triglyceride level on the 9th day.

The blood sugar and triglycerides lowering activities of the test compound was calculated accoridng to the formula:

$$\text{Blood sugar/triglycerides lowering activty}(\%) = 1 - \frac{DT/DC}{TC/ZC} \times 100$$

ZC = Zero day control group value
DC = Zero day treated group value
TC = Control group value on test day
DT = Treated group value on the test day No adverse effects were observed for any of the mentioned compounds of invention in the above test.

| Compound | Days treated | Maximum reduction in blood glucose level (%) | Triglyceride lowering (%) |
|---|---|---|---|
| Example 1 | 9 | 61* | 81 |
| Example 2 | 6 | 53 | 78 |
| Example 3 | 6 | 36 | 20 |

*daily dose: 200 mg/kg body weight

The experimental results from the db/db mice suggest that the novel compounds of the present invention also possess therapeutic utility as a prophylactic or regular treatment for obesity, cardiovascular disorders such as hypertension, hyperlipidemic and other diseases; as it is known from the literature that such diseases are interrelated to each other.

We claim:

1. A compound of the formula (I),

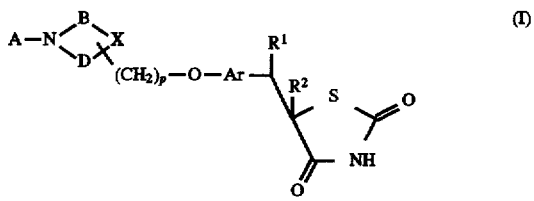

its tautomeric forms, its stereoisomers, its polymorphs, its pharmaceutically acceptable salts or its pharmaceutically acceptable solvates, where A represents a substituted or unsubstituted carbocyclic aromatic group, a substituted or unsubstituted 5-membered heterocyclic group with one heteroatom selected from oxygen, nitrogen or sulfur, or a substituted or unsubstituted six-membered heterocyclic group with one or more nitrogen atoms; B represents a substituted or unsubstituted linking group between N and X and B contains 1–4 carbon atoms; D represents a bond or D represents a substituted or unsubstituted linking group between N and X when D contains 1–4 carbon atoms; with the proviso that when the linking group B, D or both is substituted the substituent is not=O or=X represents a $CH_2$ group or a hetero atom selected from nitrogen, oxygen or sulfur; Ar represents a substituted or unsubstituted divalent aromatic or heterocyclic group; $R^1$ and $R^2$ are the same or different and represent hydrogen, lower alkyl, halogen, alkoxy or hydroxy or $R^1$ and $R^2$ taken together represent a bond and p is an integer of 0 to 4.

2. A compound according to claim 1, wherein A is substituted or unsubstituted six-membered heterocyclic group having one or more oxo group on the ring.

3. A compound according to claim 1, wherein the linking group B between N and X is saturated or contains one or more double bonds.

4. A compound according to claim 1, wherein the linking group D between N and X is saturated or contains one or more double bonds.

5. A compound as claimed in claim 1, wherein the linking group between N and X represented by B and D is saturated or contains 1–2 double bonds.

6. A compound as claimed in claim 1, wherein the aromatic group represented by A contains 1–2 rings.

7. A compound as claimed in claim 1, wherein A is a five membered heterocyclic group which contains one heteroatom selected from nitrogen, oxygen or sulfur.

8. A compound as claimed in claim 1, wherein A is a substituted aromatic group, a substituted 5-membered heterocyclic group or a 6-membered heterocyclic group, wherein the substituents are selected from hydroxy, amino, halogen, substituted or unsubstituted ($C_1$–$C_{12}$)alkyl, ($C_3$–$C_6$)cycloalkyl, cycloaminoalkyl, aryl, aralkyl, heteroaryl, alkoxy, aryloxy, alkoxycarbonyl, aryloxycarbonyl, amino ($C_1$–$C_6$)alkyl, hydroxy ($C_1$–$C_6$) alkyl, ($C_1$–$C_6$)alkoxy, thio ($C_1$–$C_6$)alkyl, ($C_1$–$C_6$)alkylthio, acyl group, carboxylic acid derivatives, acyloxy or sulfonic acid derivatives.

9. A compound as claimed in claim 8, where the substituents are substituted with halogen, lower alkyl, lower alkoxy, hydroxy or amino groups.

10. A compound as claimed in claim 1, wherein the substituents on the adjacent carbon atoms on the group represented by A form part of a substituted or unsubstituted 4–7 membered cyclic structure which is an aromatic or saturated or unsaturated carbocyclic ring or an aromatic or saturated or unsaturated heterocyclic ring wherein the hetero atoms are selected from N, O or S.

11. A compound as claimed in claim 10, wherein the substituents on the cyclic structure are selected from the group that consists of hydroxy, amino, halogen, substituted or unsubstituted ($C_1$–$C_{12}$) alkyl, ($C_3$–$C_6$)cycloalkyl, cycloaminoalkyl, aryl, aralkyl, heteroaryl, alkoxy, aryloxy, alkoxycarbonyl, aryloxycarbonyl, amino ($C_1$–$C_6$)alkyl, hydroxy ($C_1$–$C_6$) alkyl, ($C_1$–$C_6$) alkoxy, thio ($C_1$–$C_6$) alkyl, ($C_1$–$C_6$) alkylthio, acyl, carboxylic acid derivatives, acyloxy and sulfonic acid derivatives.

12. A compound as claimed in claim 1, wherein the substituents on the linking group represented by B and D are selected from the group consisting of hydroxy, amino, halogen, optionally substituted linear or branched ($C_1$–$C_{12}$) alkyl, ($C_3$–$C_6$)cycloalkyl groups, ($C_1$–$C_6$)alkoxy, ($C_3$–$C_6$) cycloalkoxy, aryl, heterocyclic groups, ($C_2$–$C_6$)acyl, ($C_2$–$C_6$)acyloxy, hydroxy($C_1$–$C_6$)alkyl, amino($C_1$–$C_6$)alkyl, mono or di($C_1$–$C_6$)alkylamino, cyclo($C_2$–$C_5$)alkylamino groups, two substituents together with the adjacent carbon atoms to which they are attached may form a substituted or unsubstituted 5–7 membered cyclic structure which may be an aromatic or saturated or unsaturated carbocyclic ring or an aromatic or saturated or unsaturated heterocyclic ring wherein the hetero atoms are selected from N, O or S and the substituents on said cyclic structure are selected from the group consisting of hydroxy, amino, halogen, substituted or unsubstituted ($C_1$–$C_{12}$)alkyl group, ($C_3$–$C_6$)cycloalkyl group, cycloaminoalkyl groups, aryl group, aralkyl, heteroaryl group, alkoxy, aryloxy, alkoxycarbonyl, aryloxycarbonyl, amino($C_1$–$C_6$)alkyl, hydroxy($C_1$–$C_6$) alkyl, ($C_1$–$C_6$)alkoxy, thio($C_1$–$C_6$)alkyl, ($C_1$–$C_6$)alkylthio, acyl group, carboxylic acid derivatives, acyloxy group, and sulfonic acid derivatives.

13. A process for the preparation of thiazolidinedione derivatives of formula (I) as defined in claim 1, their tautomeric forms, their stereoisomers, their polymorphs, their pharmaceutically acceptable salts or their pharmaceutically acceptable solvates which comprises:

a) reacting a compound of formula (V)

where A, B, D, X and p are as defined in claim 1, and $R^a$ is a hydroxy group with a compound of general formula (VI)

where Ar is as defined in claim 1, and $R^b$ is a hydroxy group or a halide group to yield a compound of formula (VII)

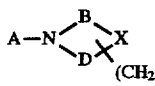 (VII)

where A, B, D, X, Ar and p are as defined earlier;
b) reacting a compound of formula (VII) obtained in step (a) with 2,4-thiazolidinedione to yield a compound of formula (VIII)

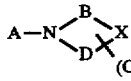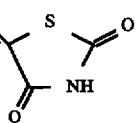 (VIII)

where A, B, D, X, Ar, and p are as defined earlier.

14. The process according to claim 13, further comprising:
reducing the compound of formula (VIII) obtained in step (b) of claim 14 to obtain the compound of formula (IX)

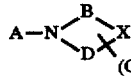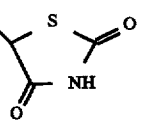 (IX)

where A, B, D, X, Ar and p are as defined in claim 14.

15. The process according to claim 13, further comprising resolving the compound of formula (VIII) into its stereoisomers.

16. The process of claim 14, further comprising resolving the compound of formula (IX) into its stereoisomers.

17. A process for the preparation of thiazolidinedione derivatives of formula (I) as defined in claim 1, their tautomeric forms, their stereoisomers, their polymorphs, their pharmaceutically acceptable salts or their pharmaceutically acceptable solvates which comprises reacting a compound of formula (V) or a compound of formula (X)

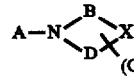 (V)

where A, B, D, X and p are as defined in claim 1, and $R^a$ is a hydroxy group

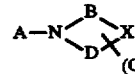 (X)

where A, B, D, X, and p are as defined in claim 1, and $L^2$ is a leaving group, with a compound of general formula (XIII)

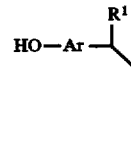 (XIII)

where $R^1$, $R^2$ and Ar are defined as in claim 1, and $R^4$ is hydrogen or a nitrogen protecting group.

18. A process for the preparation of intermediate (VII),

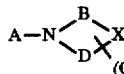 (VII)

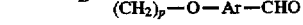

where A, B, D, X, Ar and p are as in claim 1, which comprises reacting a compound of formula (XI)

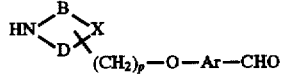 (XI)

where B, D, X, Ar and p are as defined above, with a compound of formula (III)

$A-L^1$      (III)

where A is as defined above and $L^1$ is a leaving group.

19. A process for the preparation of intermediate (VII),

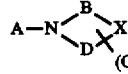 (VII)

where A, B, D, X, Ar and p are as defined in claim 1, which comprises reacting a compound of formula (X),

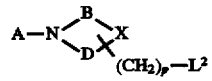 (X)

where A, B, D, X and p are as defined above and $L^2$ is a leaving group, with a compound of formula (VI)

$R^b$—Ar—CHO      (VI)

where Ar is as defined above and $R^b$ is a hydroxy group.

20. A pharmaceutical composition for the treatment or prophylaxis of diseases in which insulin resistance is the underlying pathophysiological mechanism such as type II diabetes, impaired glucose tolerance, dyslipidaemia, hypertension, coronary heart disease and other cardiovascular disorders including atherosclerosis, insulin resistance associated with obesity and psoriasis, for treating diabetic complications and other diseases such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia, which comprises a compound of the formula (I) as defined in claim 1, together with pharmaceutically acceptable carriers, diluents, or solvates.

21. A pharmaceutical composition as claimed in claim 20, in the form of a tablet, capsule, powder, syrup, solution, or suspension.

22. A method for preventing or treating diseases in which insulin resistance is underlying pathophysiological mechanism comprising administering a compound of formula (I) as defined in claim 1, and a pharmaceutically acceptable carrier, diluent or solvate to a patient in need thereof.

23. A method according to claim 22, wherein the disease is type II diabetes, impaired glucose tolerance, dyslipidaemia, hypertension, coronary heart disease, a cardiovascular disorder, atherosclerosis, insulin resistance associated with obesity and psoriasis, diabetic complications, polycystic ovarian syndrome (PCOS), renal diseases including diabetic nephropathy, glomerulonephritis, glomerular sclerosis, nephrotic 24. A compound of the formula (I),

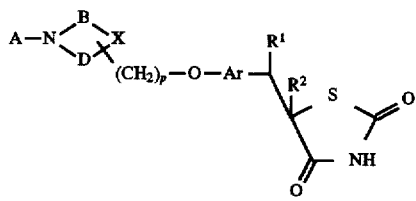

its tautomeric forms, its stereoisomers, its polymorphs, its pharmaceutically acceptable salts or its pharmaceutically acceptable solvates, where A represents a substituted or unsubstituted carbocyclic aromatic group; a substituted or unsubstituted 5-membered heterocyclic group with one heteroatom selected from oxygen, nitrogen or sulfur, or a substituted or unsubstituted six-membered heterocyclic group with one or more nitrogen atoms; B represents a substituted or unsubstituted linking group between N and X wherein B contains 1–4 carbon atoms; D represents a bond or D represents a substituted or unsubstituted linking group between N and X when D contains 1–4 carbon atoms wherein the substituents on the linking group represented by B and D are selected from the group consisting of hydroxy, amino, halogen, optionally substituted linear or branched ($C_1$–$C_{12}$) alkyl, ($C_3$–$C_6$) cycloalkyl, ($C_1$–$C_6$)alkoxy, ($C_3$–$C_6$)cycloalkoxy, aryl, heterocyclic groups, ($C_2$–$C_6$) acyl, ($C_2$–$C_6$) acyloxy, hydroxy ($C_1$–$C_6$) alkyl, amino ($C_1$–$C_6$)alkyl, mono or di ($C_1$–$C_6$) alkylamino, cyclo ($C_2$–$C_5$) alkylamino group, two substituents together with the adjacent carbon atoms to which they are attached may form a substituted or unsubstituted 5–7 membered cyclic structure which may be an aromatic or saturated or unsaturated carbocyclic ring or an aromatic or saturated or unsaturated heterocyclic ring wherein the hetero atoms are selected from N, O or S and the substituents on said cyclic structure are selected from the group consisting of hydroxy, amino, halogen, substituted or unsubstituted ($C_1$–$C_{12}$) alkyl, ($C_3$–$C_6$) cycloalkyl, cycloaminoalkyl, aryl, aralkyl, heteroaryl, alkoxy, aryloxy, alkoxycarbonyl, aryloxycarbonyl, amino ($C_1$–$C_6$) alkyl, hydroxy ($C_1$–$C_6$) alkyl, ($C_1$–$C_6$) alkoxy, thio ($C_1$–$C_6$) alkyl, ($C_1$–$C_6$) alkylthio, acyl, carboxylic acid derivatives, acyloxy, and sulfonic acid derivatives; X represents a $CH_2$ group or a hetero atom selected from nitrogen, oxygen or sulfur; Ar represents a substituted or unsubstituted divalent aromatic or heterocyclic group; $R^1$ and $R^2$ are the same or different and represent hydrogen, lower alkyl, halogen, alkoxy or hydroxy or $R^1$ and $R^2$ taken together represent a bond and p is an integer of 0 to 4.

25. A pharmaceutical composition for the treatment or prophylaxis of diseases in which insulin resistance is the underlying pathophysiological mechanism such as type II diabetes, impaired glucose tolerance, dyslipidaemia, hypertension, coronary heart disease and other cardiovascular disorders including atherosclerosis, insulin resistance associated with obesity and psoriasis, for treating diabetic complications and other diseases such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia, which comprises a compound of the formula (a) as defined in claim 24, together with pharmaceutically acceptable carriers, diluents, or solvates.

26. A pharmaceutical composition as claimed in the claim 25, in the form of a tablet, capsule, powder, syrup, solution or suspension.

27. A method for preventing or treating diseases in which insulin resistance is underlying pathophysiolocial mechanism comprising administering a compound of formula (I) as defined in claim 24, and a pharmaceutically acceptable carrier, diluent or solvate to a patient in need thereof.

28. A method according to claim 27, wherein the disease is type II diabetes, impaired glucose tolerance, dyslipideamia, hypertension, coronary heart disease, a cardiovascular disorder, atherosclerosis, insulin resistance associated with obesity and psoriasis, diabetic complications, polycystic ovarian syndrome (PCOS), renal diseases including diabetic nephropathy, glomerulonephritis, glomerular sclerosis, nephrotic syndrome, hypertensive nephrosclerosis, end-stage renal diseases, microalbuminuria, or eating disorders.

* * * * *

UNITED STATES PATENT AND TRADEMARK OFFICE
CERTIFICATE OF CORRECTION

PATENT NO. : 5,801,173
DATED : SEPTEMBER 1, 1998
INVENTOR(S) : VIDYA BHUSHAN LOHRAY, et al

It is certified that error appears in the above-indentified patent and that said Letters Patent is hereby corrected as shown below:

On title page, add -- [30] Foreign Application Priority Data

May 6, 1996 [IN] India 723/MAS/96--.

Signed and Sealed this

Eighth Day of December, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,801,173
DATED : September 1, 1998
INVENTOR(S) : Vidya Bhushan Lohray, et al.

It is certified that error appears in the above-indentified patent and that said Letters Patent is hereby corrected as shown below:

Claim 1, Column 21, line 39, before "X" insert --S;--.

Signed and Sealed this

Sixth Day of April, 1999

Attest:

Attesting Officer

Q. TODD DICKINSON

Acting Commissioner of Patents and Trademarks